US006921818B2

(12) United States Patent  (10) Patent No.: US 6,921,818 B2
Sproat  (45) Date of Patent: Jul. 26, 2005

(54) PURIFICATION OF OLIGOMERS

(75) Inventor: Brian S. Sproat, Adelebsen (DE)

(73) Assignee: Yale University, New Haven, CT (US)

( * ) Notice: Subject to any disclaimer, the term of this patent is extended or adjusted under 35 U.S.C. 154(b) by 73 days.

(21) Appl. No.: 10/627,934

(22) Filed: Jul. 25, 2003

(65) Prior Publication Data

US 2004/0044190 A1 Mar. 4, 2004

Related U.S. Application Data

(63) Continuation of application No. 09/908,042, filed on Jul. 18, 2001, now Pat. No. 6,620,926, which is a continuation of application No. 08/883,712, filed on Jun. 27, 1997, now Pat. No. 6,410,225.

(51) Int. Cl.[7] ........................ C07H 19/04; C12Q 1/68; C01B 33/08

(52) U.S. Cl. ........................ 536/26.6; 435/6; 423/342

(58) Field of Search ........................ 435/6; 536/26.6; 423/342

(56) References Cited

U.S. PATENT DOCUMENTS 5,113,005 A 5/1992 Celebuski
5,482,836 A 1/1996 Cantor et al.
6,410,225 B1 6/2002 Sproat

FOREIGN PATENT DOCUMENTS

EP 0 571 087 11/1993
WO WO 97/18312 5/1997

OTHER PUBLICATIONS

Benseler, et al., "Hammerhead–like Molecules Containing Non–Nucleoside Linkers Are Active RNA Catalysts" *J. Am. Chem. Soc.* 115:8483–8484 (1993).

Cunningham, et al., "Preparative–scale purification of RNA using an efficient method which combines gel electrophoresis and column chromatography" *Nuclei Acids Research* 24:3647–3648 (1996).

Desjardins, et al., "Pharmacokinetics of a Synthetic, Chemically Modified Hammerhead Ribozyme Against the Rat Cytochrome P–450 3A2 mRNA After Single Intravenous Injections" *J. Pharmacol. Exp. Ther.*278:1419–1427 (1966).

Fu, et al., "Hammerhead Ribozymes Containing Non–Nucleoside Linkers Are Active RNA Catalysts" *J. Am. Chem. Soc.* 116:4591–4598 (1994).

Gildea, et al., "A Versatile Acid–Labile Linker for Modification of Synthetic Biomolecules" *Tetrahedron Letters* 31:7095–7098 (1990).

Gortz & Seliger, "New Hydrophobic Protecting groups for the chemical synthesis of oligonucleotides" *Angew. Chem., Int. Ed. Engl.* 20:681 (1981).

(Continued)

*Primary Examiner*—Jezia Riley
(74) *Attorney, Agent, or Firm*—Pabst Patent Group LLP

(57) ABSTRACT

Compositions and methods are disclosed which facilitate purification of oligomers and other compounds. The disclosed compositions are silyl compositions that can be directly coupled, or coupled through a linking group, to a compound of interest, preferably to an oligomer at the end of oligomer synthesis. The silicon atom includes between one and three sidechains that function as capture tags. In one embodiment, the capture tags are lipophilic, which allows a derivatized oligomer to be separated from failure sequences by reverse phase chromatography. In another embodiment, the capture tags are compounds with a known affinity for other compounds, which other compounds are preferably associated with a solid support to allow chromatographic separation. Examples include haptens, antibodies, and ligands. Biotin, which can bind to or interact with a streptavidin-bound solid support, is a preferred capture tag of this type.

9 Claims, 4 Drawing Sheets-

OTHER PUBLICATIONS

Green, et al., "HPLC Purification of Synthetic Oligodeoxyribo-nucleotides Containing Base- and Backbone- Modified Sequences" *BioTechniques* 19:836–841 (1995).

Guo, et al., "Direct fluorescence analysis of genetic polymorphisms by hybridization with oligonucleotide arrays on glass supports", *Nucleic Acids Res.* 22:5456–5465 (1994).

Gupta, et al., "Use of the 4–methoxy–4'–octyloxytrityl group as an affinity handle for the purification of synthetic oligonucleotides" *J. Chromatogr.* 541:341–348 (1991).

Hertel, et al., "Numbering System for the Hammerhead" *Nucleic Acids Research* 20:3252 (1992).

Johnstone & Thorpe, *Immunochemistry In Practice* (Blackwell Scientific Publications, Oxford, England, 1987) pp. 209–216, 241–242, and 30–85.

Kerkhof et al., "A Comparison of Substrates for Quantifying the Signal from a Nonradiolabeled DNA Probe" *Anal. Biochem.* 205:359–364 (1992).

Langer, et al., "Enzymatic Synthesis of Biotin–Labeled Polynucleotides: Novel Nucleic Acid Affinity Probes" *Proc. Natl. Acad. Sci. USA* 78:6633 (1981).

Letsinger & Wu, "Use of a Stilbenedicarboxamide Bridge in Stabilizing, Monitoring, and Photochemically Altering Folded Conformations of Oligonucleotides" *J. Am. Chem. Soc.* 117:7323–7328 (1995).

Lyngstadaas, et al., "A synthetic, chemically modified ribozyme eliminates amelogenin, the major translation product in developing mouse enamel in vivo" *EMBO Journal* 14:5224–5229 (1995).

Mullah & Andrus, "Purification of 5'–O–Trityl–On Oligoribonucleotides. Investigation of Phosphate Migration during Purification and Detritylation" *Nucleosides & Nucleotides* 15:419–430 (1996).

Murray, et al., "A General Purification Procedure for Chemically Synthesized Oligoribonucleotides" *Analytical Biochemistry* 218:177–184 (1994).

Natt, et al., "Lipocap: a Lipophillic Phosphoramidite–based Capping Reagent" *Tetrahedron* 53(28): 9629–9636 (1997).

Olejnik, et al., "Photocleavable biotin phosphoramidite for 5'–end–labelling, affinity purification and phosphorylation of synthetic oligonucleotides" *Nucleic Acids Research* 24:361–366 (1996).

Ortigo, et al., "Antisense Effect of Oligodeoxynucleotides with Inverted Terminal Internucleotidic Linkages: A Minimal Modification Protecting against Nucleolytic Degradation" *Antisense Res. Dev.* 129–146 (1992).

Pannecoucke, et al., "Phosphodiester of 3 β (7 β–hydroxycholestreol) and of 5'(3'deoxy, 3' azido–thymidine)" *Tetrahedron* 50(4):1173–1178 (1994).

Pease, et al., "Light–generated oligonucleotide arrays for rapid DNA sequence analysis" *Proc. Natl. Acad. Sci. USA* 91(11):5022–5026 (1994).

Polushin, et al., "On the rapid deprotection of synthetic oligonucleotides and analogs" *Nucleic Acids Research* 22:639–645 (1995) *Protein immobilization: fundamentals and applications*, Richard F. Taylor, ed. (M. Dekker, New York, 1991).

Ramage & Wahl, "4–(17–Tetrabenzo[$a,c,g,i$]fluorenylmethyl)–4',4'–Dimethoxytrityl Chloride: A Hydrophobic 5'–Protecting Group for the Separation of Synthetic Oligonucleotides" *Tetrahedron Letters* 34:7133–7136 (1993).

Reddy, et al., "Methylamine Deprotection Provides Increased Yield of Oligoribonucleotides" *Tetrahedron Letters* 36:8929–8932 (1995).

Seliger & Schmidt, "Polymer Support Synthesis. XII*. Derivatization with the 4–Decyloxytrityl Group as an Aid in the Affinity Chromatography of Oligo- and Polynucleotides" *J. Chromatogr.* 397:141–151 (1987).

Seliger, et al., "Solid–Phase Oligonucleotides Synthesis with Affinity–Chromatographic Separation of the Product" *Tetrahedron Letters* 24:2115–2118 (1978).

Sinha, et al., "Polymer support oligonucleotide synthesis XVIII$^{1,2)}$: use of β–cyanoethyl–N,N–dialkylamino–/N–morpholino phosphoramidite of deoxynucleosides for the synthesis of DNA fragments simplifying deprotection and isolation of the final product" *Nucleic Acids Research* 12:4539–4557 (1984).

Sproat, et al., "An Efficient Method for the Isolation and Purification of Oligoribonucleotides" *Nucleosides & Nucleotides* 14:255–273 (1995).

Stimpson, et al., "Real–time detection of DNA hybridization and melting on oligonucleotide arrays by using optical wave guides" *Proc. Natl. Acad. Sci. USA* 92:6379–6383 (1995).

Swiderski, et al., "Polystyrene Reverse–Phase Ion–Pair Chromatography of Chimeric Ribozymes" *Analytical Biochemistry* 216:83–88 (1994).

Syvänen, et al., "Fast quantification of nucleic acid hybrids by affinity–based hybrid collection" *Nucleic Acids Res.* 14:5037 (1986).

Tsurui, et al., "Batchwise Purification of Specific tRNAs by a Solid–Phase DNA Probe" *Analytical Biochemistry* 221:166–172 (1994).

Usman, et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethionine tRNA" *J. Am. Chem. Soc.* 109:7845–7854 (1987).

Wincott, et al., "Synthesis, deprotection, analysis and purification of RNA and ribozymes" *Nucleic Acids Research* 23:2677–2684 (1995).

FIG. 2
L =
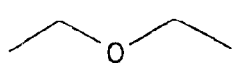
4a, 5a
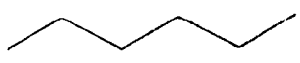
4b, 5b
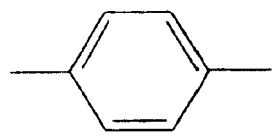
4c, 5c
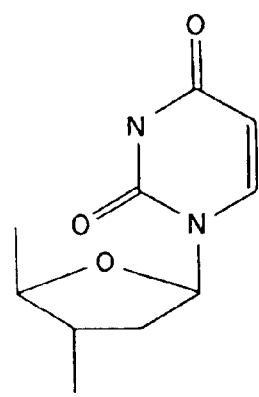
4d, 5d
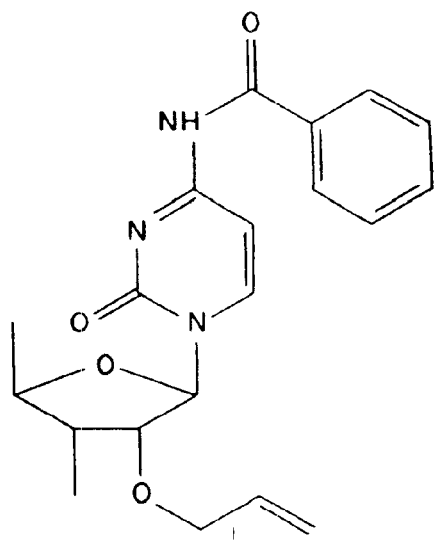
4e, 5e

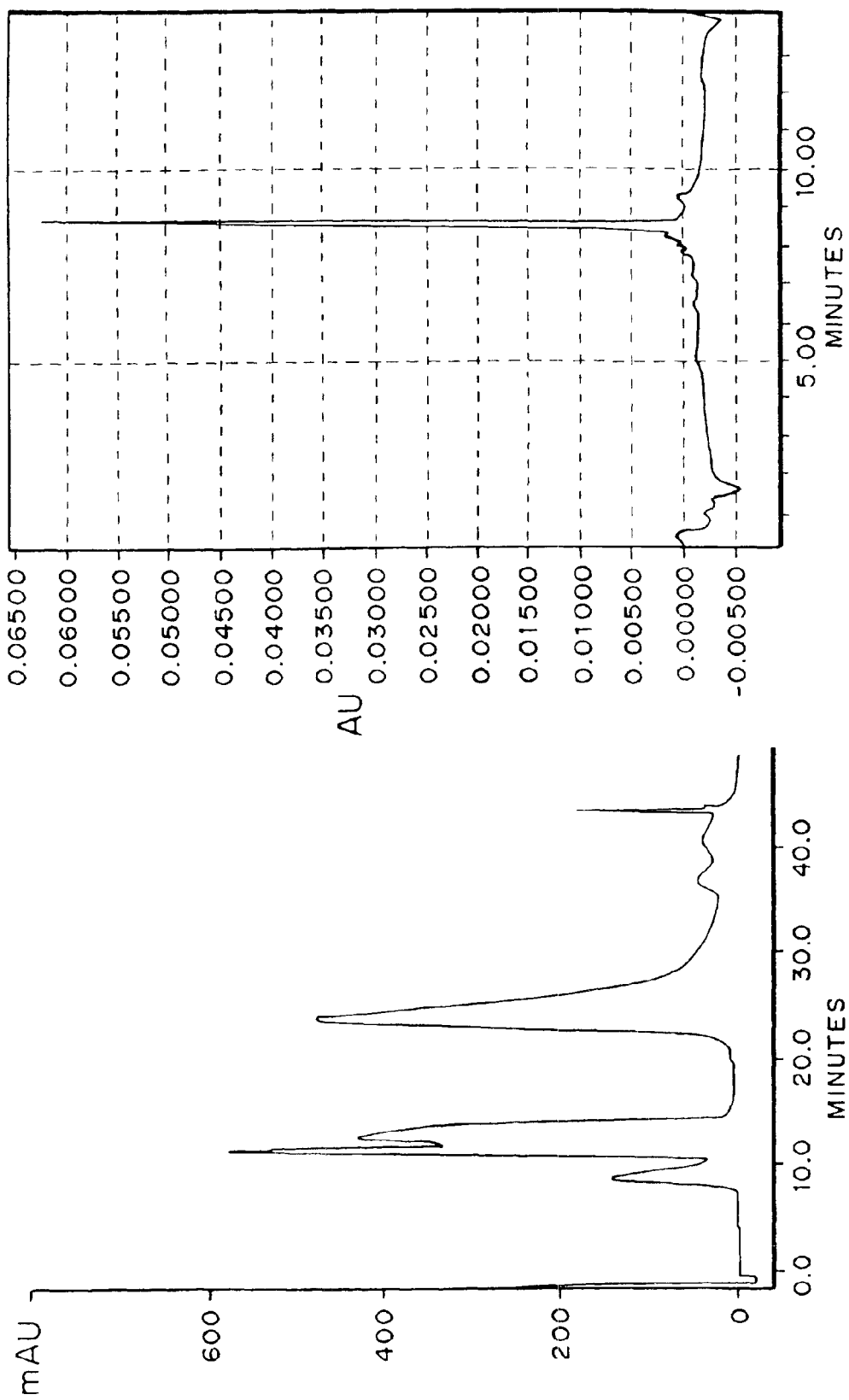

SEQUENCE LISTING

<160> NUMBER OF SEQ ID NOS: 1

<210> SEQ ID NO 1
<211> LENGTH: 35
<212> TYPE: DNA
<213> ORGANISM: Artificial Sequence
<220> FEATURE:
<223> OTHER INFORMATION: Description of Combined DNA/RNA Molecule:
      Oligonucleotide analogue
<220> FEATURE:
<223> OTHER INFORMATION: Description of Artificial Sequence: deprotected
      oligomer terminally modified with silyl
      composition

<400> SEQUENCE: 1
cagcugcuga ugaggccguu aggccgaaac aucct                                35

PURIFICATION OF OLIGOMERS

This application is a continuation of Ser. No. 09/908,042 filed Jul. 18, 2001 now U.S. Pat. No. 6,620,926 entitled "Purification of Oligomers" by Brian S. Sproat, which is a continuation of Ser. No. 08/883,712 filed Jun. 27, 1997 now U.S. Pat. No. 6,410,225.

BACKGROUND OF THE INVENTION

The disclosed invention is in the general field of oligonucleotide synthesis and purification.

Oligonucleotides are being pursued as therapeutic and diagnostic agents. Examples of such oligonucleotides include antisense oligonucleotides, aptamers, triplex forming agents, external guide sequences, catalytic oligomers, and ribozymes. Synthetic oligonucleotides based on oligo (2'-O-allylribonucleotide)s which can cleave, or induce cleavage of, specific RNA molecules are showing great promise as a new class of rationally designed therapeutics. Such chemically modified oligonucleotides are useful for cleaving an unwanted or overexpressed RNA in a highly specific fashion, thus preventing the synthesis of the corresponding protein which is causative for a particular disease state. Such an oligonucleotide having RNA cleaving activity has been successfully used in mice (Lyngstadaas et al., EMBO Journal 14:5224–5229 (1995)). Several other examples of such compounds have been shown to possess reasonable pharmacokinetics (Desjardins et al., J. Pharmacol. Exp. Ther. 278:1419–1427 (1966)). Versions of these compounds that are stable enough for in vivo applications, yet have reasonable catalytic activity, contain five residual purine ribonucleotides at critical positions in the hammerhead catalytic core and are generally in the range of 34 to 38 residues in length (Lyngstadaas et al., EMBO Journal 14:5224–5229 (1995)).

Synthetic methods for preparing oligonucleotides generally include solid phase synthesis using phosphoramidite coupling chemistry. This chemistry generally involves coupling the 3'-hydroxy group of a first nucleotide to a solid support, and reacting the 5'-hydroxy group with subsequent monomers containing protected 5'-hydroxy groups. After each coupling step, the 5'-protecting group is removed, freeing up a subsequent 5'-hydroxy group for subsequent coupling with an additional monomer. The coupling chemistry has a relatively high yield for each step, but about one to two percent of the hydroxy groups are not successfully coupled at each step in the synthesis. These un-reacted hydroxy groups must be prevented from further reactions, to avoid the preparation of unwanted sequences. To accomplish this, the hydroxy groups are capped, for example, using acetic anhydride. The capped sequences are typically referred to as failure sequences.

A major synthetic hurdle is the separation of failure sequences from the desired oligonucleotide. Current purification methodologies include anion-exchange HPLC (high pressure liquid chromatography), column chromatography, polyacrylamide gel electrophoresis, reversed phase chromatography, ion-pair chromatography, and affinity chromatography.

Purification of oligoribonucleotides and/or chemically modified ribozymes using anion-exchange chromatography with either Pharmacia Mono Q or Dionex NucleoPac columns and eluting with a salt gradient such as either sodium or lithium perchlorate has been described (Sproat et al., Nucleosides & Nucleotides 14:255–273 (1995); Wincott et al., Nucleic Acids Research 23:2677–2684 (1995)). Single base resolution of oligonucleotides, such as those described above, is typically not possible using these methods.

Additional problems associated with this purification technique are problematic secondary structure for longer RNA molecules (thus, purifications must be done at higher temperature to denature the RNA), low loading capacity, organic co-solvents such as acetonitrile are often necessary, and the columns are very expensive. Thus, the use of current ion-exchange HPLC methods is problematic even for purifying oligonucleotides on the scale of a few milligrams.

A popular method for purifying chemically synthesized oligodeoxyribonucleotides has been to leave the 5'-O-dimethoxytrityl (DMTr) protecting group on following the last coupling step of the synthesis. This protecting group functions as a lipophilic handle. The handle allows purification of full length material away from non-full length material using reversed phase HPLC because the non-full length molecules do not contain the protecting group and thus have a much less lipophilic character than the full length molecules. Unfortunately, when additional lipophilic chemical modifications are present in the oligonucleotide, or if the oligonucleotide is long (effectively increasing the lipophilicity of the non-full length molecules), undesired molecules may be more strongly retained and may even merge with the product peak, thus rendering the purification difficult or impossible. Attempts have been made to overcome this limitation by making the trityl group more lipophilic, either by adding a long alkyl or alkoxy substituent (Seliger et al., Tetrahedron Letters 2115–2118 (1978); Gortz and Seliger, Angew. Chem., Int. Ed. Engi. 20:681 (1981); Seliger and Schmidt, J. Chromatogr. 397:141–151 (1987); Gupta et al., J. Chromatogr. 541:341–348 (1991)), by adding butyl groups to all three aromatic rings of the trityl moiety, or by adding additional aromatic rings (Ramage and Wahl, Tetrahedron Letters 34:7133–7136 (1993)). In the latter case the 4-(17-tetrabenzo[a,c,g,i]fluorenylmethyl)-4', 4"-dimethoxytrityl group was employed to aid in the purification of long oligodeoxyribonucleotides greater than 100 residues in length. However, a disadvantage to this approach is that the modified trityl groups are significantly more acid labile than the standard DMTr group.

Purification of chemically synthesized oligoribonucleotides and 2'-O-methyl modified hammerhead ribozymes has been achieved by the trityl-on method followed by a second purification step by ion-exchange HPLC (Wincott et al., Nucleic Acids Research 23:2677–2684 (1995)). However, this method is very time consuming and due to the intrinsic instability of the trityl group losses occur due to premature detritylation. Furthermore, in any purification strategy the potential for product loss is increased with each successive manipulation of the product. In order for the majority of the lipophilicity of the oligonucleotide to be derived from the trityl group (which is necessary for efficient trityl based purification), the other lipophilic groups on the synthetic RNA (such as the silyl protecting groups) must be removed (Wincott et al., Nucleic Acids Research 23:2677–2684 (1995)). Unfortunately, the preferred desilylating agents, such as triethylamine trihydrofluoride, also cause loss of the DMTr group. However, this problem can be solved using triethylamine trihydrofluoride/triethylamine/N-methylpyrrolidinone which is not acidic enough to cleave the DMTr groups (Wincott et al., Nucleic Acids Research 23:2677–2684 (1995)).

Another problem associated with this method is that the oligonucleotide must be precipitated before the HPLC purification to avoid destroying the HPLC column silica matrix with the fluoride reagent used to remove the silyl groups.

Also, following purification, the trityl group must be removed under acidic conditions. Care must be taken to avoid possible acid catalyzed migration of the 3',5'-internucleotide linkages at ribose positions as well as strand cleavage (Mullah and Andrus, *Nucleosides & Nucleotides* 15:419–430 (1996)). For these reasons, the above HPLC method is not entirely satisfactory for obtaining high yields of very pure oligonucleotides.

Reverse-phase ion-pair chromatography, whereby separations are based on both hydrophobicity and on the number of anions associated with the molecule, has been used to purify fully deprotected oligoribonucleotides in a single HPLC step. However, capacity and resolution are relatively low on silica based matrices (Murray et al., *Analytical Biochemistry* 218:177–184 (1994)). New non-porous, inert polymer resins have been used to address the problem of low loading and have provided reasonable separations of oligodeoxyribonucleotides with loadings of 1 mg/ml of resin. Nonetheless, run times on the order of 2 hours are required to give adequate resolution (Green et al., *BioTechniques* 19:836–841 (1995)). Likewise, reverse-phase ion-pair chromatography on polystyrene based columns such as the PRP-1 column from Hamilton has been used to purify chemically synthesized unprotected chimeric hammerhead ribozymes (Swiderski et al., *Analytical Biochemistry* 216:83–88 (1994)). This method takes advantage of the tetrabutylammonium ions present after the desilylation reaction. Although the columns have a reasonable capacity, resolution between full length product and failure sequences differing in length by one or two residues is poor for oligonucleotides containing 38 or more residues.

Polyacrylamide gel electrophoresis can be used for the small scale purification of chemically modified ribozymes. A method for larger scale purification which combines gel electrophoresis with column chromatography has been recently described (Cunningham et al., *Nucleic Acids Research* 24:3647–3648 (1996)) and was used to purify 6.5 mg of a 34 residue ribozyme in a single run. However, the method is limited because it requires about 20 hours to complete, is limited to relatively small amounts of material, and uses relatively toxic chemicals to prepare the gels.

An alternative purification strategy is based on affinity methods, whereby a ligand-receptor interaction is utilized such as the biotin-streptavidin pair. A 5'-biotinylated oligonucleotide can be captured on an agarose column bearing covalently attached streptavidin. Assuming that the linkage between the biotin moiety and the oligonucleotide is cleavable, such as a disulfide linkage, the desired oligonucleotide can be eluted from the column by washing the column with a reagent that cleaves the linkage. In the case of a disulfide linkage, a reducing agent such as dithiothreitol or β-mercaptoethanol would be used. An alternative method using a photocleavable biotin containing moiety has also been described (Olejnik et al., *Nucleic Acids Research* 24:361–366 (1996)). Alternative oligodeoxyribonucleotides carrying a 5'-biotinylated trityl group have been affinity captured on streptavidin agarose, where the fully deprotected pure oligonucleotide is released by acid treatment (Gildea et al., *Tetrahedron Letters* 31:7095–7098 (1990)). These methods are adequate for small scale purification, but the expense of the streptavidin agarose limits their application to small scale purifications.

Another form of affinity purification uses immobilized sequences complementary to the 5'- or 3'-end of the material to be purified. Such a method has been used for the batch-wise purification of specific tRNAs (Tsurui et al., *Analytical Biochemistry* 221:166–172 (1994)). A limitation of this method is that it requires a different affinity matrix for every oligonucleotide synthesized.

It is therefore an object of the present invention to provide methods and compositions for purifying oligomeric molecules, such as oligonucleotides, without the problems associated with long purification times, acid labile protecting groups, and overlap on the column between failure sequences and the desired product peak.

BRIEF SUMMARY OF THE INVENTION

Compositions and methods are disclosed which facilitate purification of oligomers and other compounds. The disclosed compositions are silyl compositions that can be directly coupled, or coupled through a linking group, to a compound of interest, preferably to an oligomer at the end of oligomer synthesis. The silicon atom carries between one and three sidechains that function as capture tags. In one embodiment, the capture tags are lipophilic, which allows a derivatized oligomer to be separated from failure sequences by reverse phase chromatography. In another embodiment, the capture tags are compounds with a known affinity for other compounds, where the other compounds are preferably associated with a solid support to allow chromatographic separation. Examples include haptens, antibodies, and ligands. Biotin, which can bind to or interact with a streptavidin-bound solid support, is a preferred capture tag of this type.

The disclosed method involves coupling a disclosed silyl composition, including a capture tag, with a compound of interest, and separating the derivatized compound from other, non-derivatized compounds based on the properties of the capture tag. Essentially, the capture tag provides the derivatized compound with a physical or chemical property that distinguishes it from other compounds that may be present. For example, a full length oligonucleotide terminally modified with one of the disclosed silyl compositions can be more easily separated from failure sequences based on the physical or chemical properties of the capture tag which is not present on the failure sequences. Following separation, the silyl moiety can be cleaved from the oligonucleotide using standard chemistry for removing silyl groups.

In one embodiment, the silicon atom can include two or three capture tags of different types, which allows multiple separations based on the different properties of the different capture tags. This can produce material that is even more pure than that prepared using a single chromatographic separation.

The methods allow efficient purification in a one step purification process of a full length oligomer. Further, the method is fast, readily automated and is amenable to scale up.

BRIEF DESCRIPTION OF FIGURES

FIG. 2 is a diagram of the structures of examples of the L groups for the compound of FIG. 1. These are the L groups used in the lipophilic silyl compositions 5a–e used in the examples.

FIG. 3 is a preparative reversed phase HPLC trace of a "silyl-on" purification of an oligomer (SEQ ID NO:1) terminally modified with silyl composition 5b as described in Example 12.

FIG. 4 is an analytical anion-exchange HPLC trace of a fully deprotected oligomer (SEQ ID NO:1) purified as described in Example 12.

DETAILED DESCRIPTION OF THE INVENTION

Figure 1:
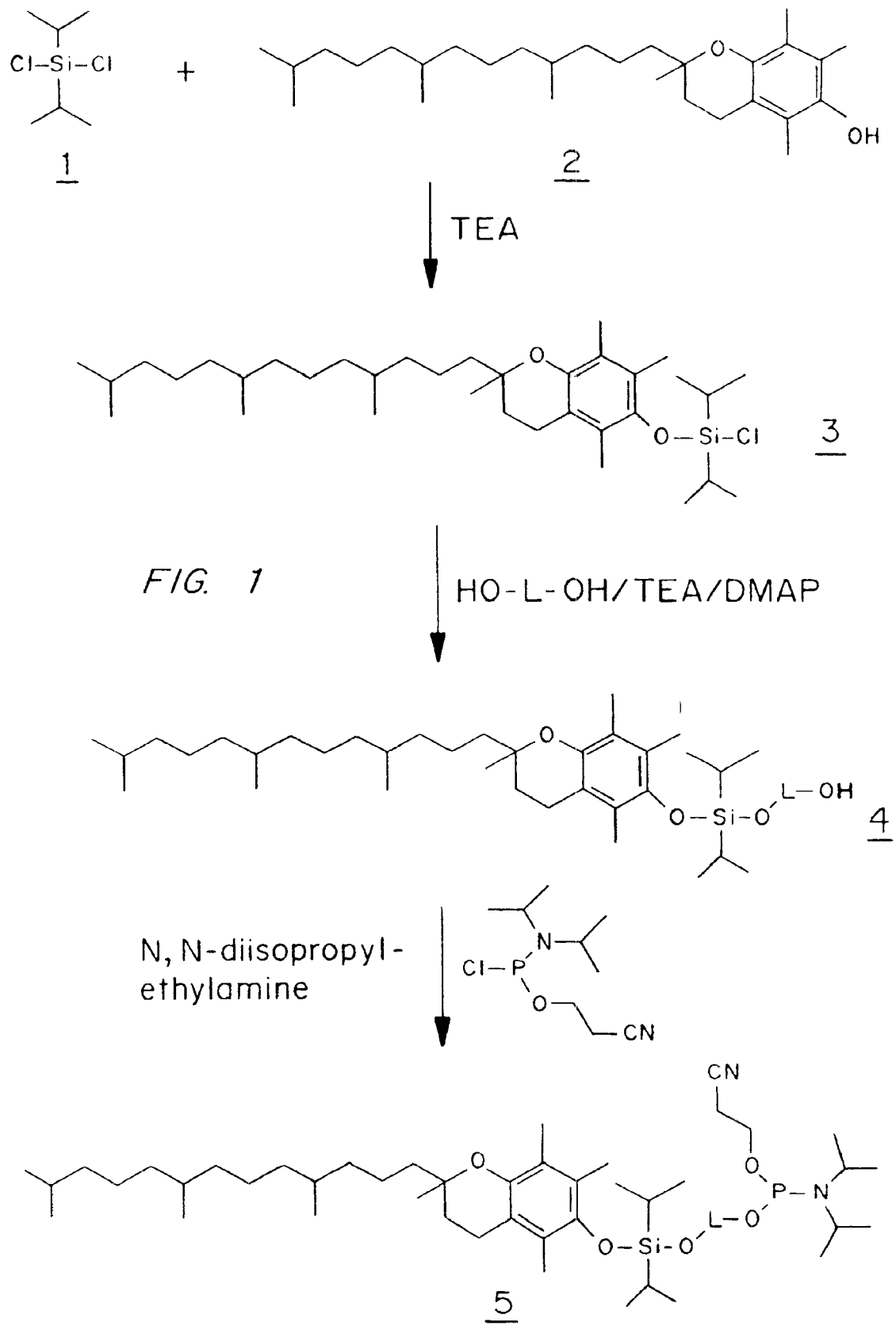
FIG. 1 is a diagram of a reaction scheme for the synthesis of an example of a silyl composition for derivatizing oligonucleotides having a lipophilic capture tag.

Compositions and methods for purifying oligonucleotides are disclosed. These compositions and methods are useful for the purification of full length products of chemically synthesized oligomers away from the non-full length or failure molecules.

The compositions and methods disclosed herein are particularly useful for purifying oligoribonucleotides because they are chemically compatible with the unique chemical functionalities associated with synthetic ribonucleotide chemistry. The 2'-hydroxyl group of ribophosphoramidites is typically protected with a modified silyl group. These protecting groups make the reversed phase HPLC separation of full length RNA difficult because the molecule is highly lipophilic. Therefore, the DMTr group does not increase the overall lipophilicity of the molecule enough to aid in the differentiation of full and non-full length product. The silyl groups must be removed prior to purification using this technique, and this is undesirable because of the intrinsic lability of the RNA phosphodiester backbone. The compositions and methods disclosed not only allow for the purification of oligomers, but they also allow for the removal of the sugar protecting groups and the purification moiety in a single step.

The disclosed compositions can be coupled to any compound of interest having a nucleophilic group. Such compounds include biomolecules, which, as used herein, refer to molecules of biologic origin, or molecules related to, or derived from, a molecule of biologic origin. As used herein, a molecule of biologic origin is a molecule synthesized by cells or organisms. Preferred compounds for coupling to the disclosed compositions include polymeric compounds that are synthesized by sequential addition of subunits. Preferred biomolecules are oligomers.

As used herein, oligomer refers to oligomeric molecules composed of subunits where the subunits can be of the same class (such as nucleotides) or a mixture of classes. Oligonucleotide refers to oligomers composed of nucleotide subunits.

Preferred oligomers include oligomeric sequences, non-nucleotide linkers, or a combination of oligomeric sequences and non-nucleotide linkers. More preferred oligomers include oligomeric sequences. Oligomeric sequences are oligomeric molecules where each of the subunits includes a nucleobase (that is, the base portion of a nucleotide or nucleotide analogue) which can interact with other oligomeric sequences in a base-specific manner. The hybridization of nucleic acid strands is a preferred example of such base-specific interactions. Oligomeric sequences preferably are comprised of nucleotides, nucleotide analogues, or both, or are oligonucleotide analogues.

Non-nucleotide linkers can be any molecule, which is not an oligomeric sequence, that can be covalently coupled to an oligomeric sequence. Preferred non-nucleotide linkers are oligomeric molecules formed of non-nucleotide subunits. Examples of such non-nucleotide linkers are described by Letsinger and Wu, (*J. Am. Chem. Soc.* 117:7323–7328 (1995)), Benseler et al., (*J. Am. Chem. Soc.* 115:8483–8484 (1993)) and Fu et al., (*J. Am. Chem. Soc.* 116:4591–4598 (1994)). Non-nucleotide linkers, or subunits for non-nucleotide linkers, include substituted or unsubstituted alkyl, alkenyl, alkynyl, alkoxy, alkenyloxy, and alkynyloxy.

As used herein, alkyl refers to substituted or unsubstituted straight, branched or cyclic alkyl groups.

As used herein, alkoxyl refers to substituted or unsubstituted straight, branched or cyclic alkoxy.

Preferably, alkyl and alkoxy groups have from 1 to 40 carbons, and more preferably from 1 to 20 carbons, from 1 to 10 carbons, or from 1 to 3 carbons.

As used herein, alkenyl refers to substituted or unsubstituted straight chain or branched alkenyl groups.

As used herein, alkynyl refers to substituted or unsubstituted straight chain or branched alkynyl groups.

As used herein, alkenyloxy refers to substituted or unsubstituted straight chain or branched alkenyloxy.

As used herein, alkynyloxy refers to substituted or unsubstituted straight chain or branched alkynyloxy.

Preferably, alkenyl, alkynyl, alkenyloxy and alkynyloxy groups have from 2 to 40 carbons, and more preferably from 2 to 20 carbons, from 2 to 10 carbons, or from 2 to 3 carbons.

As used herein, alkaryl refers to an alkyl group that has an aryl substituent.

As used herein, aralkyl refers to an aryl group that has an alkyl substituent.

As used herein, heterocyclic-alkyl refers to a heterocyclic group with an alkyl substituent.

As used herein, alkyl-heterocyclic refers to an alkyl group that has a heterocyclic substituent.

The substituents for alkyl, alkenyl, alkynyl, alkoxy, alkenyloxy, and alkynyloxy groups can be halogen, cyano, amino, thio, carboxy, ester, ether, thioether, carboxamide, hydroxy, or mercapto. Further, the groups can optionally have one or more methylene groups replaced with a heteroatom, such as O, NH or S.

As used herein, nucleoside refers to adenosine, guanosine, cytidine, uridine, 2'-deoxyadenosine, 2'-deoxyguanosine, 2'-deoxycytidine, or thymidine. A nucleoside analogue is a chemically modified form of nucleoside containing a chemical modification at any position on the base or sugar portion of the nucleoside. As used herein, the term nucleoside analogue encompasses, for example, both nucleoside analogues based on naturally occurring modified nucleosides, such as inosine and pseudouridine, and nucleoside analogues having other modifications, such as modifications to the 2' position of the sugar.

As used herein, nucleotide refers to a phosphate derivative of nucleosides as described above, and a nucleotide analogue is a phosphate derivative of nucleoside analogues as described above. The subunits of oligonucleotide analogues, such as peptide nucleic acids, are also considered to be nucleotide analogues.

Ribonucleotides and deoxyribonucleotides as used herein refer to naturally occurring nucleotides having nucleoside components adenosine, guanosine, cytidine, and uridine, or 2'-deoxyadenosine, 2'-deoxyguanosine, 2'-deoxycytidine, and thymidine, respectively, without any chemical modification. Ribonucleosides, deoxyribonucleosides, ribonucleoside analogues and deoxyribonucleoside analogues are similarly defined except that they lack the phosphate group, or an analogue of the phosphate group, found in nucleotides and nucleotide analogues.

As used herein, oligonucleotide analogues are polymers of nucleic acid-like material with nucleic acid-like properties, such as sequence dependent hybridization, that contain at one or more positions, a modification away from a standard RNA or DNA nucleotide. A preferred example of an oligonucleotide analogue is a peptide nucleic acid.

Compositions for Coupling with Oligomers

The compositions disclosed herein are silicon-containing compositions capable of being covalently coupled with nucleophilic groups, such as hydroxy groups, amine groups or carboxy groups, on compounds of interest, either directly or via a linking group. These silyl compositions include one or more capture tags which allow the compound to which the silyl composition has been coupled to be purified based on the capture tag. Such purification is preferably accomplished by, for example, chromatographic separation using a column which interacts differently with the capture tag than with compounds not coupled to one of the silyl compositions.

The disclosed compositions have the following general formula:

$$D\text{-}Si(Y)_3$$

Compositions of this form are preferably reagents which can be coupled to a hydroxyl group on a compound of interest. In this case, D represents a leaving group, a leaving group coupled to a linking group, a reactive group, or a reactive group coupled to a linking group. A leaving group is a group that can be displaced by a nucleophile, such as a hydroxy group, amine group, or carboxylate group. A reactive group is a group that can be attacked by a nucleophile.

Compositions of the form D-Si(Y)$_3$ also include the products of the coupling of the above reagents to a compound of interest. In this case, D represents either the compound of interest (directly coupled to the silicon atom), or the compound coupled to a linking group (through which the compound is coupled to the silicon atom).

Thus, in the formula D-Si(Y)$_3$, D represents X-, X-Z-, V-, V-Z-, W, or W-Z-, where X is a compound of interest, Z is a linking group, V is a leaving group, and W is a reactive group.

Any leaving group can be used which can be displaced by a hydroxy group on a compound of interest under conditions that do not adversely affect the compound. Suitable leaving groups include iodide, bromide, chloride, tosylate, nosylate, mesylate, triflate, brosylate, and acetate.

Any reactive group can be used which can be reacted with a hydroxy group on a compound under conditions that do not adversely affect the compound. Preferred reactive groups include activatable phosphorus moieties such as phosphoramidites or active moieties such as phosphochloridates. An activatable phosphorus moiety as used herein is any phosphorus derivative which can react with a nucleophile such as a 5'-hydroxyl. Preferred activatable phosphorus moieties are P(OR$^6$)(NR$^4$R$^5$), P(R$^7$)(NR$^4$R$^5$), P(H)(O)(O$^-$), P(O)(O$^-$)(OR$^6$), where R$^4$ and R$^5$ are alkyl groups which may be the same or different, or which together form part of a ring structure, R$^6$ is a standard phosphate protecting group, R$^7$ is an alkyl, aryl or aralkyl moiety and may be branched and be optionally substituted.

The use of an activatable phosphorus moiety in the disclosed compositions is highly preferred because such compositions can be attached via nucleophilic attack of the activatable phosphorus moiety by the 5'-hydroxyl of the oligomer. An attachment of this type is preferred because when the silyl moiety is removed, a 5'-derivatized phosphate is left attached to the oligomer and this will inhibit 5'-exonuclease digestion of the oligomer.

Any linking group can be used which can be coupled to a hydroxy group on a compound under conditions that do not adversely affect the compound. Suitable linking groups are substituted or unsubstituted C$_{1-20}$ straight, branched or cyclic alkyl, aralkyl, aryl, alkaryl, alkenyl, alkynyl, alkoxy, alkenyloxy, alkynyloxy, heteroalkyl, heterocyclic, alkyl-heterocyclic, or heterocyclic-alkyl. Preferred substituents are hydroxy, thio, amine, ether, thioether, keto, carboxy, alkenyl, alkynyl, phosphorus derivatives, or carbonyl. One or more of the carbons in the linking group can be replaced by O, S, or NH. Preferred linking groups are derived from diols.

Preferred linking groups have the formula

—B-L-B— where each B is, independently, O, S, or NH, and where L is substituted or unsubstituted C$_{1-20}$ straight, branched or cyclic alkyl, aralkyl, aryl, alkaryl, alkenyl, alkynyl, alkoxy, alkenyloxy, alkynyloxy, heteroalkyl, heterocyclic, alkyl-heterocyclic, or heterocyclic-alkyl. Preferred substituents are hydroxy, thio, amine, ether, thioether, keto, carboxy, alkenyl, alkynyl, phosphorus derivatives, or carbonyl. One or more of the carbons in L can be replaced by O, S, or NH.

Each Y is independently a capture tag or substituted or unsubstituted C$_{1-20}$ straight, branched or cyclic alkyl, aralkyl, aryl, alkaryl, alkenyl, alkynyl, alkoxy, alkenyloxy, alkynyloxy, heteroalkyl, heterocyclic, alkyl-heterocyclic, or heterocyclic-alkyl. At least one Y is a capture tag. Preferred substituents are hydroxy, thio, amine, ether, thioether, keto, carboxy, alkenyl, alkynyl, phosphorus derivatives, or carbonyl. One or more of the carbons in Y can be replaced by O, S, or NH. It is preferred that Y is not a trityl group.

Capture Tags

As used herein, a capture tag is any compound that can be associated with a compound of interest, and which can be used to separate compounds associated with the capture tag from those not associated with the capture tag. For use with the disclosed compositions and methods, capture tags are part of the disclosed composition.

Preferred capture tags include ligands, haptens; oligonucleotides, antibodies, and lipophilic molecules.

Ligands and Haptens

One preferred form of capture tag is a compound, such as a ligand or hapten, that binds to or interacts with another compound, such as a ligand-binding molecule or an antibody. It is preferred that such an interaction between the capture tag and the capturing component be a specific interaction, such as between a hapten and an antibody or a ligand and a ligand-binding molecule.

Suitable capture tags include hapten or ligand molecules that can be coupled to the 5'-end of an oligonucleotide molecule. Preferred capture tags, described in the context of nucleic acid probes, have been described by Syvanen et al., *Nucleic Acids Res.* 14:5037 (1986)). Preferred capture tags include biotin, which can be incorporated into nucleic acids (Langer et al., *Proc. Natl. Acad. Sci. USA* 78:6633 (1981)) and captured using streptavidin or biotin-specific antibodies. A preferred hapten for use as a capture tag is digoxigenin (Kerkhof, *Anal. Biochem.* 205:359–364 (1992)). Many compounds for which a specific antibody is known, or for which a specific antibody can be generated, can be used as capture tags. Such capture tags can be captured by antibodies which recognize the compound. Antibodies useful as capture tags can be obtained commercially or produced using well established methods. For example, Johnstone and Thorpe, *Immunochemistry In Practice* (Blackwell Scientific Publications, Oxford, England, 1987), on pages 30–85, describe general methods for producing both polyclonal and monoclonal antibodies.

Anti-Antibodies

Another preferred capture tag is one which can be used in an anti-antibody method. Such anti-antibody-antibodies and their use are well known. In these methods, the hapten for the anti-antibody is an antibody. For example, anti-antibody-antibodies that are specific for antibodies of a certain class (for example, IgG, IgM), or antibodies of a certain species (for example, anti-rabbit antibodies) are commonly used to detect or bind other groups of antibodies. Thus, an antibody to the capture tag can be reacted with the capture tag and the resulting antibody:capture tag:oligomer complex can be purified by binding to an antibody for the antibody portion of the complex.

Selectively Cleavable Compounds

Compounds that form selectably cleavable covalent bonds with desired molecules can also be used as capture tags. For example, a preferred capture tag of this type is one which contains a sulfur atom. Such a capture tag is referred to herein as a thiol containing moiety or residue. A compound associated with this capture tag, such as an oligomer, can be purified, for example, by retaining the oligomer on an activated thiopropyl Sepharose column, removing contaminating compounds, such as failure sequences, that are not retained on the column, and reducing the disulfide linkage, for example, with β-mercaptoethanol. This method allows the desired compound to be collected after purification under relatively mild conditions.

Lipophilic Molecules

The most preferred form of capture tag is a lipophilic molecule. Lipophilic molecules, as used herein, are those molecules which, when associated with a compound of interest (that is when coupled to the compound as part of a disclosed composition), allow the compound to be base line separated from contaminating compounds using reverse phase HPLC. In the case of oligomers, a lipophilic molecule is molecule which, when coupled to a full length oligomer as part of a disclosed composition, allows the full length oligomer to be base line separated from the failure sequences (that is, less than full length oligomers) using reverse phase HPLC. Lipophilic molecules present in the disclosed compositions are referred to as lipophilic residues. Preferred lipophilic capture tags are tocopheryl, cholesteryl and long chain alkyl groups.

Making and Using the Disclosed Compositions

The disclosed silyl compositions can be made using standard nucleophilic displacements. In a preferred embodiment (see FIG. 1 and Examples 1 through 11) diisopropyldichlorosilane (1) is first reacted with a suitable highly lipophilic alcohol such as cholesterol or tocopherol, more commonly known as vitamin E (2), and the crude monochlorosilane (3) is further reacted with a simple diol such as 1,6-hexanediol, diethylene glycol or benzene-1,4-dimethanol or a complex diol such as a partially protected nucleoside (see FIG. 2 for the structures of L in the compositions used in the examples). The reaction product, of general structure (4), is purified by chromatography and the remaining hydroxyl function is phosphitylated, for example with 2-cyanoethoxy N,N-diisopropylaminochlorophosphine to give a phosphoramidite reagent (5) suitable for use in solid phase synthesis by the β-cyanoethyl phosphoramidite approach (Sinha et al., *Nucleic Acids Research* 12:4539–4557 (1984)). The silyl phosphoramidite reagent can then be used in a standard oligonucleotide coupling step using standard activating reagents and solvents.

Particularly preferred are linking groups based on 1,6-hexanediol. Desilylation after the HPLC purification of oligomers synthesized with such a lipophilic silyl moiety leaves the linking group attached to the 5'-end of the oligomer and serves to protect the compound against 5'-exonuclease degradation. If a free 5'-hydroxyl is desired, a silyl composition having a leaving group but no linking group (such as compound 3 in FIG. 1) can be coupled to the 5'-hydroxyl of an oligomer. After purification, desilylation results in regeneration of a free 5'-end on the oligomer.

The use of highly labile nucleobase protecting groups on the oligomer, such as tert-butylphenoxyacetyl, is preferred since it reduces premature desilylation which would lead to some strand cleavage, since rapid deprotection is carried out either with aqueous ammonia/ethanol or with alternative more efficient reagents such as methylamine/ethanol (Reddy et al., *Tetrahedron Letters* 36:8929–8932 (1995); Wincott et al., *Nucleic Acids Research* 23:2677–2684 (1995)) or ethanolamine/methanol (Polushin et al., *Nucleic Acids Research* 22:639–645 (1995)).

The disclosed compositions can be coupled to a compound of interest using chemistry that is well known to those of skill in the art, for example, amidations, esterifications, and nucleophilic displacement chemistry. The coupling of the disclosed silyl compositions to compounds of interest is preferably accomplished through standard nucleophilic displacement, or via an activatable group, such as a phosphoramidite, attached to the silyl moiety.

It is preferred that the disclosed compositions be used as terminal modifiers in oligomer synthesis. During each of the successive coupling steps of an oligomer synthesis (for example, oligonucleotide synthesis), approximately 98–99% of the growing oligomer chain is actually extended by the addition of the next subunit. Those molecules not extended are capped (typically with acetic anhydride or tert-butylphenoxyacetic anhydride) to prevent molecules which have internal deletions from being formed. Often, the amount of full length product is less than 25% of the crude product.

At the end of synthesis, the full length product is substantially the only product with a terminal hydroxy group that is not capped as an acetate, which also means that it contains the only free hydroxy group available for subsequent modification. This allows coupling of the disclosed silyl compositions only to the full length oligomer at the end of synthesis and not to any failure sequence. In this way, the capture tag on the silyl composition renders the full length oligomer physically or chemically different from the less than full length oligomers.

After the oligomers are coupled with the compositions, they are brought into contact with a substrate that binds to or interacts with the capture tag(s) in a different manner than it binds to or interacts with failure sequences (which lack capture tags). The different interaction or binding allows separation of the failure sequences from the full length oligomer. The silyl composition can then be removed to generate the desired oligomer.

To allow interaction of the oligomer with the substrate, the substrate includes a moiety, referred to herein as a capture tag receptor, which interacts with the capture tag.

Capture Tag Receptors (CTR)

After association of one of the disclosed compositions (containing a capture tag) with a compound of interest, the derivatized compound is selectively isolated from the molecules which are not associated with the capture tag (for example, failure sequences in oligomer synthesis). The derivatized compound is selectively isolated by a specific interaction between the capture tag and a molecule which binds the capture tag, referred to herein as a capture tag receptor (CTR). CTRs are preferably associated with a solid support. When compounds associated with capture tags are bound to CTRs of this type they can be effectively purified from the unwanted molecules because the solid support allows for successive washing to remove unbound molecules.

Solid Supports

Supports for CTRs can be any solid material to which the CTRs can be adhered or coupled. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Supports can have any useful form including thin films or membranes, beads, bottles, dishes, fibers, woven fibers, shaped polymers, particles and microparticles. Preferred forms of supports are plates and beads. The most preferred form of beads are magnetic beads.

Methods for immobilizing oligonucleotides on supports are well established. Oligonucleotides or oligonucleotide derivatives can be coupled to substrates using established coupling methods. For example, suitable attachment methods are described by Pease et al., *Proc. Natl. Acad. Sci. USA* 91(11):5022–5026 (1994), and Khrapko et al., *Mol Biol (Mosk) (USSR)* 25:718–730 (1991). A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state supports is described by Guo et al., *Nucleic Acids Res.* 22:5456–5465 (1994). Oligonucleotides can act as CTRs by interacting (that is hybridizing) with oligomers having a defined sequence.

Methods for immobilizing antibodies on solid-state supports are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidinbiotin, photocrosslinkable agents, epoxides and maleimides. A preferred attachment agent is glutaraldehyde. These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209–216 and 241–242, and *Immobilized Affinity Ligands*, Craig T. Hermanson et al., eds. (Academic Press, New York, 1992). Antibodies can be attached to a support by chemically cross-linking a free amino group on the antibody to reactive side groups present within the solid-state support. For example, antibodies may be chemically cross-linked to a support that contains free amino or carboxyl groups using glutaraldehyde or carbodiimides as crosslinking agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

In addition, non-antibody proteins such as streptavidin can be linked using similar methods. Many protein and antibody columns are commercially available as well as specifically derivatized supports for conjugation to the CTRs.

Chemically modified CTRs such as thiopropyl Sepharose are commercially available or they can be made using standard conjugation chemistry such as cyanogen-bromide coupling or the equivalent.

Another preferred CTR for use with lipophilic capture tags is a reversed phase HPLC column. Preferred types of reversed phase HPLC columns are based on polystyrene, examples of which are the PRP-1 column sold by Hamilton and the Source 15 RPC column sold by Pharmacia.

Removal of the Compositions

The disclosed compositions link capture tags to compounds of interest via silyl containing moieties. The silyl moieties act much like a bridge between the capture tag and the compound. The benefit of this bridge is that it is readily removable in the same process used for the removal of the 2'-O silyl protecting groups on synthesized oligomers. Thus, not only can the capture tag be removed from an oligomer after purification, but the removal takes place during normal desilylation of the oligoribonucleotide. The silyl group can be removed using standard techniques well known to those of skill in the art, for example, reaction with fluoride ions.

The compositions and methods will be further understood from the following non-limiting examples.

EXAMPLES

Example 1

Diisopropyl(DL-α-tocopheryloxy)chlorosilane (3)

A solution of DL-α-tocopherol (21.5 g, 50 mmol) in dichloromethane (100 ml) was added dropwise over 30 minutes to a solution of diisopropyldichlorosilane (9.05 ml, 50 mmol) and triethylamine (7.65 ml, 55 mmol) in dichloromethane (500 ml) at 0° C. under anhydrous conditions, and the reaction was then allowed to reach room temperature and was stirred for 1 to 3 days. The solvent was evaporated in vacuo and petrol/diethylether (200 ml, 1:1 v/v) was added to the residue and stirred until the oil dissolved and the triethylamine hydrochloride precipitated. The hydrochloride was filtered off and washed with petrol/diethylether (1:1 v/v) and the filtrate evaporated in vacuo to an oil, which was dissolved to a standard volume in dichloromethane. The combined organics were used directly without purification and assuming a quantitative reaction for the ensuing experiments.

Example 2

1-[Diisopropyl(DL-α-tocopheryloxy)silyl]oxy-5-hydroxy-3-oxapentane (4a)

Diethyleneglycol (4.76 ml, 50 mmol) was dissolved in dichloromethane (125 ml) and triethylamine (2 ml, 15 mmol), and 4-dimethylaminopyridine (183 mg, 1.5 mmol) were added. To this solution was added compound 3 (10 mmol in dichloromethane, see above) and the reaction was stirred overnight at room temperature with exclusion of moisture. The solvent was evaporated in vacuo and the residue dissolved in dichloromethane, washed with aqueous sodium bicarbonate solution, dried (sodium sulfate), filtered and evaporated to dryness in vacuo. Purification on a column of silica gel (3×15 cm) eluting with petrol/ethyl acetate (3:1 v/v) gave compound 4a (2.83 g, 44%) as an almost colorless oil ($R_f$ 0.61 on silica gel TLC in petrol/ethyl acetate (2:1 v/v)). $^{13}C$ NMR spectrum ($CDCl_3$), δ: 145.83, 144.61, 124.91, 122.52, 122.19, 116.92 and 77.62 (tert. Cs DL-a-tocopheryl), 39.44, 39.18, 37.20 (4Cs), 31.56, 24.60, 24.21 and 20.75 (2Cs)($CH_2$s toco.), 32.55, 32.41 and 27.74 (CHs toco.), 23.46, 22.48, 22.39 and 19.45 (2Cs), 13.58, 12.66 and 11.70 (CH$_3$s toco.), 72.33 and 72.09 (C-2, C-4), 62.65 and 61.43 (C-1, C-5), 17.00 (isopropyl CH$_3$s) and 12.66 p.p.m. (isopropyl CHs).

Example 3

1-[Diisopropyl(DL-α-tocopheryloxy)silyl]oxy-6-hydroxyhexane (4b)

1,6-Hexanediol (14.77 g, 125 mmol), triethylamine (5.2 ml, 37.5 mmol) and 4-dimethylaminopyridine (460 mg, 3.75 mmol) in dichloromethane (100 ml) and N,N-dimethylformamide (25 ml) were reacted with compound 3 (25 mmol) and worked up as described for compound 4a above. Purification on a silica gel column (5×13 cm) eluting with petrol/ethyl acetate (4:1 v/v) gave compound 4b (7.3 g, 44%) as an almost colorless oil ($R_f$ 0.83 on silica gel TLC in petrol/ethyl acetate (2:1 v/v)). $^{13}$C NMR spectrum (CDCl$_3$), δ: 145.82, 144.91, 125.16, 122.76, 122.30, 117.11, and 74.28 (tert. Cs toco.), 39.52, 39.32, 37.35 (4Cs), 31.73, 24.74, 24.36 and 20.91 (2Cs) (CH$_2$s toco.), 32.66 (2C) and 27.88 (CHs toco.), 23.62, 22.60 (2Cs), 19.60 (2C), 13.72, 12.84 and 11.86 (CH$_3$s toco.), 63.18 (C-1), 62.56 (C-6), 32.54 (C-2 and C-5), 25.53 (C-3 and C-4), 17.26 (isopropyl CH$_3$s) and 12.84 p.p.m. (isopropyl CHs).

Example 4

1-[Diisopropyl(DL-α-tocopheryloxy)silyloxy]methyl-4-hydroxymethylbenzene (4c)

1,4-Bis(hydroxymethyl)benzene (6.9 g, 50 mmol), triethylamine (2 ml, 15 mmol) and 4-dimethylaminopyridine (183 mg, 1.5 mmol) in dichloromethane (100 ml) and N,N-dimethylformamide (25 ml) were reacted with compound 3 (10 mmol) and worked up as described for compound 4a above. Purification on a column of silica gel (5×15 cm) eluting with petrol/ethyl acetate (4:1 v/v) gave compound 4c (3.64 g, 53%) as an almost colorless oil of $R_f$ 0.77 on silica gel TLC in petrol/ethyl acetate (2:1 v/v). $^{13}$C NMR spectrum (CDCl$_3$) δ: 145.88, 144.76, 125.07, 122.69, 122.33, 117.10 and 74.23 (tert. Cs toco.), 39.47, 39.28, 37.31 (4Cs), 31.66, 24.71, 24.32, and 20.86 (2Cs) (CH$_2$s toco.), 32.65, 32.52 and 27.84 (CHs toco.), 23.55, 22.56 (2Cs), 19.55 (2Cs), 13.71, 12.89 and 11.81 (CH$_3$s toco.), 139.88, 139.63 (phenyl C-1 and C-4), 126.70 (2Cs), 125.85 (2Cs) (phenyl C-2, C-6 and C-3, C-5) 64.55 (CH$_2$s phenyl), 17.26 (isopropyl CH$_3$s) and 12.89 p.p.m. (isopropyl CHs).

Example 5

5'-O-[Diisopropyl(DL-α-tocopheryloxy)silyl]thymidine (4d)

Thymidine (1.21 g, 5 mmol), triethylamine (2 ml, 15 mmol) and 4-dimethylaminopyridine (183 mg, 1.5 mmol) in dichloromethane (50 ml) and N,N-dimethylformamide (50 ml) were reacted with compound 3 (10 mmol) for 24 h at room temperature and worked up as described for compound 4a above. Purification on a silica gel column (5×10 cm) eluting with petrol/ethyl acetate/dichloromethane (from 4:2:1 to 2:2:1 v/v/v) gave compound 4d (2.18 g, 55%) as an almost colorless oil of $R_f$ 0.32 on silica gel TLC in petrol/ethyl acetate (1:1 v/v). $^{13}$C NMR spectrum (CDCl$_3$) δ: 164.15 (C-4), 150.62 (C-2), 135.29 (C-6), 110.81 (C-5), 86.84 (C-1'), 84.46 (C-4'), 71.19 (C-3'), 63.18 (C-5'), 40.68 (C-2'), 11.76 (CH$_3$ of thymine), 145.97, 144.36, 124.73, 122.42 (2Cs), 117.20 and 74.30 (tert. Cs toco.), 39.52, 39.14, 37.16 (4Cs), 31.43, 24.58, 24.21 and 20.76 (2Cs) (CH$_2$s toco.) 32.53, 32.10 and 27.74 (CHs toco.), 23.38, 22.50, 22.40, 19.46 (2Cs), 13.72, 12.51 and 12.01 (CH$_3$s toco.), 17.07 (isopropyl CH$_3$s) and 12.75 p.p.m.(isopropyl CHs).

Example 6

5'-O-[Diisopropyl(DL-α-tocopheryloxy)silyl]-N$^4$-benzoyl-2'-O-allylcytidine (4e)

N$^4$-Benzoyl-2'-O-allylcytidine (1.36 g, 3.6 mmol), triethylamine (0.75 ml, 5.4 mmol) and 4-dimethylaminopyridine (66 mg, 0.54 mmol) in dichloromethane (50 ml) and N,N-dimethylformamide (10 ml) were reacted with compound 3(0.6 mmol) for 24 h at room temperature and worked up as described for compound 4a above. Purification on a column of silica gel (3×13 cm) eluting with petrol/ethyl acetate/dichloromethane (6:3:1 v/v/v) gave compound 4e (1.11 g, 33%) as an almost colorless semi-solid foam ($R_f$ 0.33 on silica gel TLC in petrol/ethyl acetate (1:1 v/v)). $^{13}$C NMR spectrum (CDCl$_3$) δ: 166.57 (C=O benzoyl), 162.94 (C-4), 154.97 (C-2), 143.72 (C-6), 132.70 (C-1 phenyl), 133.44 (CH allyl) 132.08 (C-4 phenyl), 127.89, 127.44 (C-2, C-6, C-3, C-5 phenyl), 116.69 (CH$_2$ allyl) 95.90 (C-5), 88.29 (C-1'), 83.06 (C-4'), 80.81 (C-2'), 70.27 (CH$_2$ allyl), 66.28 (C-3'), 60.06 (C-5'), 145.53, 143.89, 124.29, 122.03, 121.87, 116.83 and 73.67 (tert. Cs toco.), 39.01, 38.66, 36.68 (4Cs), 30.97, 24.12, 23.72 and 20.17 (2Cs) (CH$_2$s toco.), 32.04, 31.92 and 27.25 (CHs toco.), 22.01, 21.93, 20.17, 18.98 (2Cs), 13.21, 12.04 and 11.30 (CH$_3$s toco.), 16.84 and 16.56 (isopropyl CH$_3$s), 12.27 and 12.04 p.p.m. (isopropyl CHs).

Example 7

1-[Diisopropyl(DL-α-tocopheryloxy)silyl]oxy-5-(2-cyanoethoxy N,N-diisopropylaminophosphinoxy)-3-oxapentane (5a)

Compound 4a (2.83 g, 4.36 mmol) was dried by several evaporations of anhydrous toluene in vacuo, then dissolved in dichloromethane (75 ml) under argon and N,N-diisopropylethylamine (2.3 ml, 13.1 mmol) was added and the solution was cooled in an ice-bath. 2-Cyanoethoxy N,N-diisopropylaminochlorophosphine (1.16 ml, 5.23 mmol) was added slowly via a syringe and the reaction was stirred at 0° C. under anhydrous conditions. After 45 min TLC on silica gel plates pre-run in petrol/ethyl acetate (2:1 v/v) containing 2% triethylamine to avoid decomposition of the product showed complete reaction with a new spot of $R_f$ 0.90. The reaction was diluted with dichloromethane, washed with aqueous sodium bicarbonate solution, dried (sodium sulfate), filtered and evaporated to dryness in vacuo. Purification on a florisil column (5×10 cm) eluting with petrol/ethyl acetate (4:1 v/v) containing 1% triethylamine afforded compound 5a (3.15 g, 85%) as a colorless oil. $^{31}$P NMR spectrum (CDCl$_3$) δ: 146.20 p.p.m.

Example 8

1-[Diisopropyl(DL-α-tocopheryloxy)silyl]oxy-6-(2-cyanoethoxy N,N-diisopropylaminophosphinoxy)hexane (5b)

Compound 4b (7.3 g, 11 mmol) was phosphitylated with 2-cyanoethoxy N,N-diisopropylaminochlorophosphine (2.91 ml, 13.2 mmol) N,N-diisopropylethylamine (5.7 ml, 33 mmol) and in dichloromethane (100 ml) and worked up as described for compound 5a above. Purification on a florisil column (5×13 cm) eluting with petrol/ethyl acetate (4:1 v/v) containing 1% triethylamine afforded compound 5b (7.7 g, 81%) as a colorless oil ($R_f$ 0.9 on silica gel TLC in petrol/ethyl acetate (2:1 v/v)) containing 2% triethylamine. $^{31}$P NMR spectrum (CDCl$_3$) δ:145.13 p.p.m.

Example 9

1-[Diisopropyl(DL-α-tocopheryloxy)silyloxy]methyl-4-[(2-cyanoethoxy N,N-diisopropylaminophosphinoxy)methyl]benzene (5c)

Compound 4c (3.64 g, 5.34 mmol) was phosphitylated with 2cyanoethoxy N,N-diisopropylaminochlorophosphine (1.42 ml, 6.4 mmol) and N,N-diisopropylethylamine (2.78 ml, 16 mmol) in dichloromethane (50 ml) and worked up as described for compound 5a above. Purification on a column of florisil (5×13 cm) eluting with petrol/ethyl acetate (4:1 v/v) containing 1% triethylamine afforded compound 5c (2.69 g, 57%) as a colorless oil of $R_f$ 0.9 in petrol/ethyl acetate (2:1 v/v) containing 2% triethylamine. $^{31}$P NMR spectrum (CDCl$_3$) δ: 146.24 p.p.m.

Example 10

5'-O-[Diisopropyl(DL-α-tocopheryloxy)silyl]thymidine-3'-O-(2-cyanoethyl N,N-diisopropylphosphoramidite) (5d)

Compound 4d (1.74 g, 2.2 mmol) was phosphitylated with 2-cyanoethoxy N,N-diisopropylaminochlorophosphine (663 μl, 3 mmol) and N,N-diisopropylethylamine (1.03 ml, 6 mmol) in dichloromethane (30 ml) and worked up as described for compound 5a above, but using room temperature and a reaction time of 1.5 h. Purification on a column of silica gel (3×12 cm) eluting with petrol/ethyl acetate/dichloromethane (6:2:1 to 4:2:1 v/v/v) containing 1% triethylamine afforded compound 5d (1.78 g, 82%) as a colorless semi-solid foam ($R_f$ 0.52 and 0.47 on silica gel TLC in petrol/ethyl acetate (1:1 v/v) containing 2% triethylamine). $^{31}$P NMR spectrum (CDCl$_3$) δ: 146.38 and 146.22 p.p.m.

Example 11

5'-O-[Diisopropyl(DL-α-tocopheryloxy)silyl]-N$^4$-benzoyl-2'-O-allylcytidine-3'-O-(2-cyanoethyl N,N-diisopropylphosphoramidite) (5e)

Compound 4e (1.11 g, 1.075 mmol) was phosphitylated with 2-cyanoethoxy N,N-diisopropylaminochlorophosphine (0.33 ml, 1.5 mmol) and N,N-diisopropylethylamine (0.52 ml, 3 mmol) in dichloromethane (10 ml) and worked up as described for compound 5d above. Purification on a column of silica gel (3×13 cm) eluting with petrol/ethyl acetate (2:1 v/v) containing 1% triethylamine afforded compound 5e (1.1 g, 90%) as an almost colorless semi-solid foam ($R_f$ 0.33 on silica gel TLC in petrol/ethyl acetate (1:1 v/v)). $^{31}$P NMR spectrum (CDCl$_3$) δ: 148.07 and 147.26 p.p.m.

Example 12

Synthesis, Deprotection and Purification of Oligomers Based on the Hammerhead Ribozyme 2'-O-Allyl modified oligomers based on the Gerlach type hammerhead ribozyme and containing five residual purine ribonucleotides (that is G5, A6, G8, G12 and A15.1 based on the standard numbering system (Hertel et al., *Nucleic Acids Research* 20:3252 (1992))) necessary for cleavage activity and also stabilized at the 3'-terminus for in vivo use (Lyngstadaas et al., *EMBO Journal* 14:5224–5229 (1995)) were synthesized by solid-phase β-cyanoethyl phosphoramidite chemistry (Sinha et al., *Nucleic Acids Research* 12:4539–4557 (1984)) on a Perkin Elmer/Applied Biosystems DNA/RNA synthesizer model 394 using the 2'-O-tert.butyldimethylsilyl (TBDMS) protection strategy for the ribonucleotides (Usman et al., *J. Am. Chem. Soc.* 109:7845–7854 (1987)). Syntheses were performed on either aminopropyl controlled pore glass or aminomethylpolystyrene bearing an inverted thymidine linkage (Ortigao et al., *Antisense Res. Dev.* 129–146 (1992)) or alternative modification to protect the final oligomers against degradation by 3'-exonucleases. 5'-O-Dimethoxytrityl-2'-O-allylribonucleoside-3'-O-(2-cyanoethyl N,N-diisopropylphosphoramidites) and 5'-O-dimethoxytrityl-2'-O-tert.butyldimethylsilylribonucleoside-3'-O-(2cyanoethyl N,N-diisopropylphosphoramidites) bearing tert.butylphenoxyacetyl protection of the exocyclic amino functions of adenine, cytosine and guanine were obtained from PerSeptive Biosystems (Hamburg, Germany). Syntheses of oligomers of desired sequence were generally performed on a 1 μmol scale using a standard RNA cycle except for a cap-oxidize-cap procedure following each monomer addition. Capping was performed using the Expedite cap mixture supplied by PerSeptive Biosystems.

After adding the last desired 2'-O-allylribonucleotide at the 5'-end of the oligomer a further synthesis cycle was performed using one of the general lipophilic handles, that is, monomer 5a, 5b or 5c used as a 0.1 M solution in acetonitrile/dichloromethane (1:1 v/v) and coupled using the standard 1H-tetrazole solution for 15 min (FIG. 2). Following the cap-ox-cap part of the cycle the column was washed thoroughly with acetonitrile and blown dry and the oligomer was cleaved from the support and all base labile protecting groups (2-cyanoethyl and 4-tert.butylphenoxyacetyl) were removed by treatment with ethanolamine/ethanol (0.5 ml, 1:1 v/v) for 2 h at 60° C. This procedure leaves all the silyl groups intact.

The full length product was purified by reversed phase HPLC on a Pharmacia Åkta-Explorer 10 system using a Hamilton PRP-1 7×305 mm column as follows:—Buffer A was 0.1 M triethylammonium acetate, pH 7.5 in water/acetonitrile (9:1 v/v) and buffer B was 0.1 M triethylammonium acetate in water/acetonitrile (1:19 v/v). The supernatant containing the silyl protected oligomer was diluted with aqueous 0.1 M triethylammonium acetate/acetonitrile to give an organic composition more or less equivalent to 50% B and loaded immediately onto the PRP-1 column. Elution was performed at 4 ml/min with 50% B for 1.5 column volumes (CV), then 50-89% B for 0.5 CV and held at 89% B for 0.75 CV to elute the desired product. FIG. 3 shows a representative HPLC trace of a "silyl on" purification done at 4 μmol scale using a 21.5×250 mm column run at 8 ml/min. The product peak at about 25 minutes is clearly separated from the non-derivatized molecules contained in the peak eluting at about 12 minutes. The column was then washed with 100% B for 0.5 CV and then re-equilibrated at 50% B for 1 CV. Monitoring of the column effluent was performed at 260 and 295 nm. The product peak, eluting at about 80% B (about 10 min after starting the run for the 7×305 mm column) was collected in a sterile Eppendorf tube and lyophilized on a Speedvac. The pellet was then dissolved in 300 μl of anhydrous triethylamine/triethylamine tri(hydrofluoride)/N-methylpyrrolidinone (3:4:6 v/v/v) and kept at 60° C. for 4 h to cleave the silyl protecting groups (Wincott et al., *Nucleic Acids Research* 23:2677–2684

Figure 5:
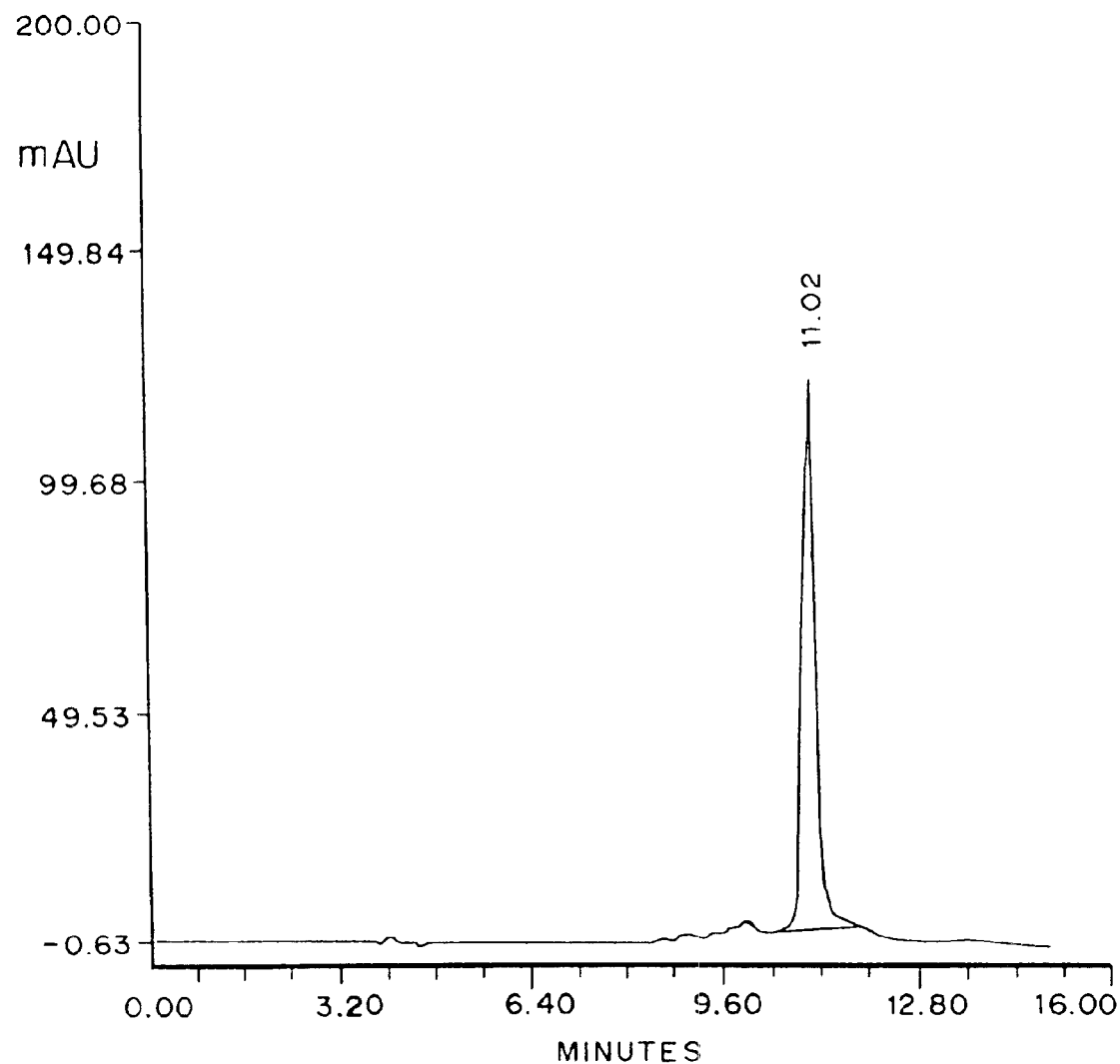
FIG. 5 is a dynamic sieving capillary electropherogram of a fully deprotected oligomer (SEQ ID NO:1) purified as described in Example 12.

(1995)). The deprotected oligomer was then precipitated by adding sterile aqueous 3 M sodium acetate (30 µl, pH 5.2) followed by 1-butanol (1 ml). The Eppendorf tube was kept at −20° C. for 15 minutes and the precipitate was collected by centrifugation at 6000 rpm for 5 minutes. The pellet was washed once with acetone (1 ml), dried in a Speedvac and then redissolved in sterile water (100 µl). To this solution was added 5 M aqueous sodium perchlorate (150 µl) followed by acetone (1.35 ml) and after vortexing, the tube was kept for 30 minutes at −20° C. The precipitated sodium salt of the oligomer was then collected by centrifugation for 10 minutes at maximum speed and washed twice with acetone to remove traces of sodium perchlorate and finally dried in a Speedvac. The oligomer was then dissolved in sterile water (500 µl) and desalted by passage through a sterile NAP-5 column from Pharmacia Biotech. The void volume from the column containing the pure sodium salt of the oligomer was then dried in a Speedvac and the residue washed once with acetone (1 ml) to give a fluffy white pellet after drying. The isolated yields of oligomers obtained this way are in the range of 2.5 to 4 mg from a 1 µmol scale synthesis. The oligomer, the purification and analysis of which is illustrated in FIGS. 3, 4 and 5, is a catalytic oligomer having the nucleotide sequence SEQ ID NO: 1 whereby all nucleotides are 2'-O-allylribonucleotides except for the five essential ribonucleotides required for maintaining catalytic activity (Lyngstadaas et al., *EMBO Journal* 14:5224–5229 (1995)). Chimeric oligomers capable of targeting structural motifs in RNA thereby inducing cleavage as described in WO 97/18312 were also purified using the synthesis modification described herein.

The quality of the fully deprotected purified material was then checked both by analytical anion-exchange HPLC and dynamic sieving capillary electrophoresis. Anion-exchange HPLC was performed on a Dionex Nucleopac PA-100 column (4×250 mm) at 55° C. using a gradient of sodium perchlorate in 25 mM Tris-HCl/1 mM EDTA pH 7.0 in water/acetonitrile (9:1 v/v) run at 2 ml/min and monitoring by UV at 260 nm. Buffers A and B contained 10 mM and 500 mM sodium perchlorate respectively. The following gradient conditions were used:

8% B for 2 min;
8 to 23% B during 0.5 min;
23% B for 1 min;
23 to 65% B during 6 min;
65 to 100% B during 0.25 min;
100% B for 1.25 min;
100–8% B during 0.25 min; and
8% B for 2 min to re-equilibrate the column prior to the next run.

FIG. 4 shows a representative anion-exchange HPLC tracing of a fully deprotected oligomer (SEQ ID NO:1).

Dynamic sieving capillary electrophoresis was performed on a BioFocus 3000 TC capillary electrophoresis system (BIO-RAD Labs., Munich, Germany) using the following conditions:

75 µm ID×24 cm coated capillary (part no. 148–3080) temperature controlled at 40° C.;

dynamic sieving buffer (part no. 148–5026) plus 8 M urea;

run conditions: 10 kV, constant voltage, polarity − to + during 15 minutes;

injection: electrokinetic 5 kV for 8 sec;

detection: UV at 260 nm.

FIG. 5 shows a representative electropherogram of a fully deprotected oligomer (SEQ ID NO:1).

Publications cited herein and the material for which they are cited are specifically incorporated by reference.

Those skilled in the art will recognize, or be able to ascertain using no more than routine experimentation, many equivalents to the specific embodiments of the compositions and methods described herein. Such equivalents are intended to be encompassed by the following claims.

What is claimed is:

1. A method of synthesizing a compound of the formula 1

$$Y'—Si(Y)_2\text{-B-L-B-W} \qquad (1),$$

where each B independently is O, S or NH,

L and each Y independently is C1-20 straight, branched or cyclic alkyl, aralkyl, aryl, alkaryl, alkenyl, alkynyl, alkoxy, alkenyloxy, alkynyloxy, heteroalkyl, heterocyclic, alkyl-heterocyclic, or heterocyclic-alkyl, Y' is a capture tag, and W is a reactive group;

the method comprising
(a) reacting a dihalosilane with Y'-E, where E is a leaving group;
(b) coupling the product of (a), a monohalosilane, with a compound of the formula B-L-B; and
(c) reacting the product of (b) with W to form the compound of formula 1.

2. The method of claim 1 wherein Y'-E is a lipophilic alcohol.

3. The method of claim 2 wherein the lipophilic alcohol is selected from the group consisting of cholesterol or tocopherol.

4. The method of claim 1 wherein both Bs are O.

5. The method of claim 4 wherein L is selected from the group consisting of diethyleneglycol, 1,6-hexandiol, 1,4-bis(hydroxymethyl)benzene, thymidine and N4-benzoyl-2'-O-allylcytidine.

6. The method of claim 1 wherein each Y is lower alkyl.

7. The method of claim 6 wherein the dihalosilane is diisopropyldichlorosilane.

8. The method of claim 1 wherein the halogen of the monohalosilane is displaced with a compound of the formula B-L-B.

9. The method of claim 8 wherein W is 2-cyanoethoxy-N,N-diisopropylaminochlorophosphine.

* * * * *